United States Patent
Loosveld

(10) Patent No.: US 10,492,464 B2
(45) Date of Patent: Dec. 3, 2019

(54) LIVESTOCK FARMING SYSTEM

(71) Applicant: LELY PATENT N.V., Maassluis (NL)

(72) Inventor: Serge Louis Loosveld, Maassluis (NL)

(73) Assignee: LELY PATENT N.V., Maassluis (NL)

( * ) Notice: Subject to any disclaimer, the term of this patent is extended or adjusted under 35 U.S.C. 154(b) by 338 days.

(21) Appl. No.: 15/316,781

(22) PCT Filed: Jun. 24, 2015

(86) PCT No.: PCT/NL2015/050456
§ 371 (c)(1),
(2) Date: Dec. 6, 2016

(87) PCT Pub. No.: WO2016/010417
PCT Pub. Date: Jan. 21, 2016

(65) Prior Publication Data
US 2017/0202177 A1    Jul. 20, 2017

(30) Foreign Application Priority Data

Jul. 15, 2014    (NL) .................................... 2013189

(51) Int. Cl.
*A01K 5/02* (2006.01)
*A01K 5/00* (2006.01)
(Continued)

(52) U.S. Cl.
CPC .............. *A01K 5/02* (2013.01); *A01D 41/127* (2013.01); *A01K 5/001* (2013.01); *A01K 29/00* (2013.01);
(Continued)

(58) Field of Classification Search
CPC ...... A01K 5/002; A01K 5/005; A01K 5/0275; A01K 5/02; A01K 5/001; A01K 29/00;
(Continued)

(56) References Cited

U.S. PATENT DOCUMENTS 7,441,515 B2 * 10/2008 Renz ...................... A01K 29/00
    119/174
8,655,751 B2 * 2/2014 Renz .................. G06Q 10/0875
    119/51.01

(Continued)

FOREIGN PATENT DOCUMENTS

| EP | 1 212 938 A1 | 6/2002 |
| WO | WO 2010/071413 A2 | 6/2010 |
| WO | WO 2012/023124 A2 | 2/2012 |

*Primary Examiner* — Tien Q Dinh
*Assistant Examiner* — Brady W Frazier
(74) *Attorney, Agent, or Firm* — Birch, Stewart, Kolasch & Birch, LLP

(57) ABSTRACT

A livestock farming system for use in connection with feed for livestock and including at least one livestock-related device to carry out a livestock-related action on the feed and a controller to control the livestock farming system and generate information messages, and with a communication system. The livestock farming system is configured to define a parameter value relating to the condition of the person, and the controller is configured to send communication messages with the communication system and/or make cognizable said messages to the person depending on the defined parameter value. Since the livestock farming system can assess the condition of the receiving person, the system can make a choice in the sending and/or communicating of the information to the person, so that it can be better guaranteed that the information to be sent will be effectively processed, and is not disregarded or incorrectly processed because the person is, for example, suffering from a high level of stress.

20 Claims, 1 Drawing Sheet

(51) Int. Cl.
*A01K 29/00* (2006.01)
*G08B 21/02* (2006.01)
*A01D 41/127* (2006.01)
*A61B 5/00* (2006.01)
*A61B 5/0205* (2006.01)
*H04L 12/18* (2006.01)
*A61B 5/021* (2006.01)
*A61B 5/024* (2006.01)
*A61B 5/06* (2006.01)
*A61B 5/08* (2006.01)
*A61B 5/16* (2006.01)

(52) U.S. Cl.
CPC .......... *A61B 5/0022* (2013.01); *A61B 5/0205* (2013.01); *A61B 5/6887* (2013.01); *G08B 21/02* (2013.01); *A61B 5/021* (2013.01); *A61B 5/024* (2013.01); *A61B 5/067* (2013.01); *A61B 5/0816* (2013.01); *A61B 5/165* (2013.01); *H04L 12/1895* (2013.01)

(58) Field of Classification Search
CPC ... A61B 5/0022; A61B 5/0205; A61B 5/6887; A61B 5/024; A61B 5/067; A61B 5/165; A61B 5/021; A61B 5/0816; G08B 21/02; H04L 12/1895; A01D 41/127
USPC ....... 340/506, 539.1, 573.3; 700/90; 702/19, 702/166; 703/11; 726/3; 455/41.1; 40/300; 119/51.01, 51.02, 51.11, 51.13, 119/51.14, 51.15
See application file for complete search history.

(56) References Cited

U.S. PATENT DOCUMENTS

| | | |
|---|---|---|
| 2003/0146834 A1 | 8/2003 | Stevens et al. |
| 2005/0076839 A1* | 4/2005 | Van Den Berg ........ A01J 5/017 119/14.04 |
| 2014/0116341 A1* | 5/2014 | Kopic .................... A01K 29/00 119/14.02 |

* cited by examiner

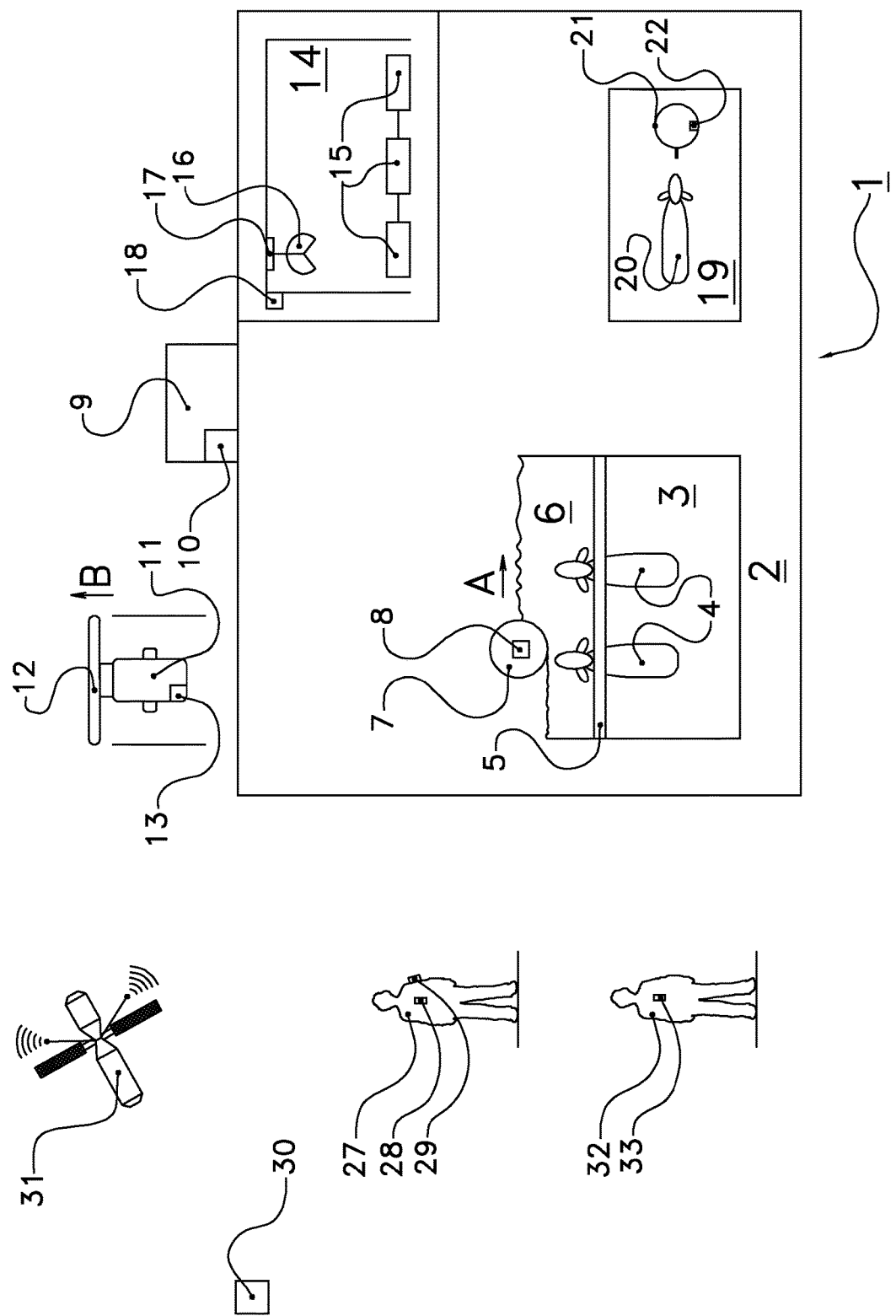

LIVESTOCK FARMING SYSTEM

The invention relates to a livestock farming system for use with livestock and comprising at least one livestock-related device which is configured to carry out a livestock-related action, in particular on one or more of the livestock, and a controller to control the livestock farming system and generate information messages, and with a communication system comprising a first communication device which is at least configured to send the information messages, and a second communication device which is at least configured to receive the information messages that have been sent by the first communication device and make them cognizable to a person.

Livestock farming systems of this type are known per se. Examples include milking robots and other automata which, in the event of a fault or the like, send an alarm message to a receiver of an operator who, as a result, does not always have to be present. On receiving an alarm or other message, the operator can then take action, if desired.

In practice, the efficiency of a system of this type, wherein information such as alarms is forwarded to operators or other persons, turns out not always to be optimal. This may have the result that the forwarded information is not processed, is not processed adequately or is processed too late, which can have disadvantageous consequences for the livestock and/or parts of the livestock farming system.

An object of the present invention is therefore to provide an improved livestock farming system which at least offers the possibility to handle the information messages more efficiently.

For this purpose, the invention provides a livestock farming system according to claim 1, in particular a livestock system for use in a livestock building environment for livestock and comprising at least one livestock-related device which is configured to carry out a livestock-related action, in particular on one or more of the livestock, and a controller to control the livestock farming system and generate information messages, and with a communication system comprising a first communication device which is at least configured to send the information messages, and a second communication device which is at least configured to receive the information messages that have been sent by the first communication device and make them cognizable to a person, wherein the livestock farming system is configured to define a parameter value of a parameter relating to the condition of the person, and wherein the controller is configured to send the information message and/or make it cognizable to the person depending on the defined parameter value.

Here, the invention makes use of the insight that the person who receives and has to process the message is not always readily able to do so. There may be many different reasons and causes for the inability of the person, as will be explained in detail below, but the present system can take account of this in the manner in which the information message is transferred to the receiving person, so that it can at least be better guaranteed that the information arrives and can be processed in an optimum manner. It is important to note that the present invention does not relate to settings with which, or a system wherein, the user himself actively sets his communication device to "do not disturb", or forwards it to voicemail, a different number or the like. For example, the user thus runs the risk instead that alarm messages or the like are received unnecessarily late because the "do not disturb" setting is cancelled too late. An active operation on the part of the user is also required for both setting and cancelling/modifying the setting, which is not always desirable. In the present invention, on the other hand, the livestock farming system itself is configured to determine how the information message will be transferred, i.e. depending on the parameter defined by the system. It is again noted that this does not mean that the system only establishes that the user/receiver has set his communication device to "do not disturb", "forward" or the like, but that the system decides, on the basis of a parameter that is not to be actively forwarded by the user/receiver, how to send the information message. In addition, it is obviously still an option for the controller to comprise a "do not disturb" mode, wherein information messages are either not received (and, for example, a message such as a spoken message is returned), or are held and only later communicated. In an embodiment of this type it is also clear that the present invention is more than a "do not disturb" mode given that, even if the "do not disturb" mode is not activated, information messages can be held, delayed or the like, but now depending on this defined parameter value. It should be noted that it may furthermore be possible for the second mode of the controller to be deactivatable by the user, so that in this condition the controller, i.e. the livestock farming system, operates as a system from the prior art, apart from this switchability.

The communication system comprises a first communication device for sending information and a second communication device for receiving the information. Obviously, it is also possible, but not necessary, for communication to take place from the second to the first communication device. The second communication device can be physically connected here to other parts of the controller, in particular the first communication device, such as with a wire. Examples of second communication devices of this type are, for example, a computer, such as a management computer, or a fixed telephone to which a spoken SMS message or the like can be sent. However, it is preferably a communication device that is wirelessly connected or connectable to the first communication device. Further details of this aspect will be given below.

In the present invention, the livestock farming system comprises at least one autonomous feed-related device for carrying out a livestock-related action on the feed. In the present invention, a feed-related action is understood to mean an action that is carried out on feed or for the purpose of producing feed. Devices of this type will also become increasingly autonomous, i.e. they will be able to perform their task without continuous human supervision. The reasons for this are, for example, efficiency and scaling-up, but the consequence may be that certain risks arise in the feed provisioning. In any case, there is less human supervision than previously in the case of manual operations. However, avoidance of such risks is of great importance precisely in the case of devices for carrying out feed-related actions. At any rate, the livestock are directly, and humans therefore indirectly, dependent on a guaranteed quality of their feed. In any case, therein lies a part of the importance of the present invention, i.e. to ensure as far as possible, even without direct human supervision, that any information messages such as alarms are received and processed by a supervising person in the best possible manner.

In principle, an autonomous device is not, or at least not entirely, supervised. For this reason, it may occur relatively more frequently that a person responsible for supervising the livestock farming system, or at least the autonomous device, is occupied with another activity or task, or is otherwise unable to process the information message in an optimum manner. Autonomous devices of this type are often complex devices which also have to cope with variable and in most cases unpredictable live animals, and can therefore send a multiplicity of information messages, the interpretation of which sometimes requires a little, but sometimes also a great deal of attention. The present invention can then at least partially prevent the information message from being incorrectly disregarded in that the manner of sending and/or making cognizable said message is adapted to the established condition of the receiving person.

In embodiments, the autonomous feed-related device comprises a harvester such as a mower or thresher, or a feed gate, a feed-combining device, a feed-mixing device and/or a feed-dispensing device. Devices of this type may, for example, autonomously harvest or produce feed, such as through mowing or threshing. This may involve a completely autonomous device or a device that moves autonomously, but follows another vehicle, such as a harvester. It may also involve an autonomous vehicle that pushes feed into a livestock building, such as a Lely Juno™, or a device or vehicle that combines, mixes or otherwise processes feed and/or supplies it to the animals, such as a Lely Vector™ or Lely Calm™ automatic calf feeder, but also feed-providing machines for chickens, pigs and other livestock. All of these autonomous feed-related devices, and of course certainly the animals that are dependent on these devices, benefit from the invention.

In embodiments, the controller is configured to send the information message from the first communication device to the second communication device and to make cognizable the information message on the second communication device to the person in a first mode for non-delayed communication to the second communication device if the defined parameter value meets a first criterion, and to send the message from the first communication device to the second communication device and/or make said message cognizable to the person on the second communication device in a second, different mode if, and in particular as long as, the defined parameter value meets a second, different criterion. In the first mode, the information message is thus forwarded as quickly as possible to the person, both in terms of sending the information message from the first to the second communication device and in terms of communicating the information message to the person on the second communication device, such as with a readable or audible signal or message. In fact, the forwarding therefore relates to forwarding to the second communication device, but it is assumed here that the second communication device is actually located with the intended person, so that the person receives the information. Otherwise the advantage of the invention is at any rate barely appreciable. Here, "as quickly as possible" means that no intentional delays are built in, unlike those imposed by the prior art, such as transfer rate and speed of internal processing of the information. Intentional delay means, for example, the collection of messages by the communication system or the controller as a whole in order to forward these messages once per fixed period, such as an hour. In the first mode, the information message is thus delivered to the intended person as quickly as possible. This will be advantageous if the defined parameter value meets the first criterion, which is chosen in such a way that the likelihood is great that the receiving person is readily able to process the information message in an optimum manner.

If the defined parameter value does not meet the first criterion and if, and in particular as long as, the second criterion, which is, for example, not exclusively complementary to the first criterion, is met, the controller will send the information message from the first communication device to the second communication device and/or make said message cognizable to the person on the second communication device, in the second, different mode. The controller switches over to this second mode if it appears from the defined parameter value that the likelihood is great, or at any rate sufficiently greater, that the receiving person cannot process the information message efficiently enough. The livestock farming system can thus take account of the fact that the receiver cannot respond in an optimum manner. How and under what conditions the livestock farming system, and, in particular, the controller, respond will be explained in detail below.

In embodiments, the first criterion comprises that the defined parameter value has a predefined value or lies in a predefined interval, and the second criterion comprises that the parameter value does not have the predefined value or lies outside that interval, in particular lies in a second interval. By means of a parameter of this type, the livestock farming system can then make a distinction in order to choose the correct mode. It should be noted that the number of modes could also be extended to three or more, with a corresponding number of criteria. The parameter value can relate here to a physical value, but also a relative or even abstract value, such as "person is busy", though a value of this type will in most cases be determined on the basis of one or more physical values. Furthermore, the interval may be unlimited on one or even both sides. In this last case, the first criterion requires that the parameter value lies outside a limited interval. However, the interval will often be limited on both sides. The interval may relate to a real interval, such as with physical values, or may also comprise natural or whole number values or a collection of abstract values.

In embodiments, the controller is configured in the second mode to delay sending the information message from the first communication device or communicating the information message to the person until either the defined parameter value meets the first criterion, or until a third criterion is met. In this way, it can be sufficiently guaranteed that the information message is processed efficiently. The third criterion may, for example, comprises that one or more of the defined parameter values improves to a predefined extent, i.e. the exceeding of a limit value decreases relatively or absolutely to a predefined extent.

In embodiments, the controller is configured in the second mode to send the message to a different, third communication device. Thus, if it is likely that the information message will be uncertainly processed by the receiving person, the controller can choose to send the information message to an alternative person, i.e. a third communication device. It should be noted that this does not include the parameter or situation wherein a telephone call or the like is forwarded if a telephone line or other communication line is busy. It involves a parameter of the person, not the terminal itself.

In embodiments, the controller is configured to send information messages with different priority, such as pure information, alert signals and alarm signals, and the controller is configured to send the information messages from the first communication device to the second communication device or to make said messages cognizable on the second communication device depending on the priority. In estimating whether and how efficiently the information can be processed, the controller takes account of the possible impact of the information message. Thus, with expected moderate attention, a purely informative message will probably be disregarded, but an alarm will actually be processed.

It may then be appropriate to defer the sending of the purely informative message until the sending of an alarm, since concentration and attention will possibly have improved thereafter. Obviously, some monitoring can also be carried out by means of the parameter values to be defined.

In embodiments, the parameter is a physical condition parameter of the person, and the livestock farming system comprises a sensor actively connected to the controller to measure the parameter value of the person. This sensor, or one of the sensors, is, for example, provided close to the controller or the livestock-related device, but, in particular, on the second communication device so that the sensor is usually close to the intended person, i.e. the carrier of the second communication device. A physical condition parameter is chosen here as the parameter. These parameters can provide a clear estimation relating to the concentration of the person, or the extent to which incoming information messages can be efficiently processed. However, measurement of different or additional parameters is not excluded. The sensor is actively connected to the controller, such as directly communicating with the controller, or to the second communication device or otherwise. For example, the sensor forms part of the second communication device, but that is not obligatory. It may, for example, comprise a camera with image recognition which is configured to determine a concentration level, indicatively or relatively or otherwise, from the physical characteristics, such as the posture of the head and body, facial expression, speed of movement, etc. Systems of this type are known per se, for example from the automotive sector. The camera can be provided on the tablet or laptop computer or smartphone, but also, for example, in a livestock building or office. The camera may be person-tracking.

It is furthermore noted here that the controller may be self-learning, wherein the controller is configured to adjust at least the first criterion on the basis of responses to information messages that have been made cognizable to the person in the past. If, in the case of a specific parameter value, for example a given information message that required timely or even immediate action but was disregarded, the controller can conclude that the measured parameter value still fell in an interval wherein the concentration of the user was insufficient. The edges of the interval for the first criterion can then be actively adjusted accordingly by the controller.

In embodiments, the parameter comprises a stress level parameter, in particular an acceleration, a heart rate, a blood pressure and/or a respiration frequency, and the sensor comprises an accelerometer, a heart rate monitor, a blood pressure monitor and/or a respiration frequency monitor. Alternative or additional parameters are operating speed and/or precision and/or force of the second communication device, and the sensor comprises a keystroke speed monitor and/or keystroke precision monitor and/or keystroke force monitor. Particularly in the case of modern operating interfaces with a touch screen, this is an attractive design. A high stress level is a clear indication that the receiving person is less able to process the information message correctly and/or in a timely manner. A stress level of this type can be measured in many ways, and, in particular, by means of the indicated sensors. For example, a heart rate monitor can be provided which measures the heart rate of the person. If or as long as the heart rate is above a defined limit value according to a first criterion, the controller can for example, delay sending the message. The accelerometer measures whether the person is subject to accelerations. This may in fact be an indication of agitated movements or otherwise, such as running, driving or the performance of all manner of actions. Situations of this type are indicative of a reduced concentration level in relation to incoming information messages. It is noted here that the accelerometer, if installed in the second communication device, actually measures the accelerations of this second communication device, but it is assumed here that the accelerations of the person are comparable. Furthermore, it is noted that the aforementioned sensors may also be provided separately on the person, such as a heart rate monitor (of the type known from fitness aids), a blood pressure or respiration frequency monitor. Alternatives are certainly conceivable, such as on the basis of facial recognition or a direction of view sensor, of the type already known per se from the automotive industry for detecting drowsiness of a driver. A stress level can also be derived from the manner of operation. If the number of keystrokes or the keystroke force is higher than an absolute threshold value, or, for example, a relative threshold value linked to an average, which may be a running average or otherwise, for the person operating the second communication device, this can be a clear indication of an increased stress level. The controller can then decide to switch over to the second mode.

In embodiments, the parameter value comprises an ambient parameter value of the person, in particular a sound pressure level around the person or a position of the person. This parameter value may be an alternative or additional indication of the concentration of the person. The person will thus be able to receive, register and/or process the information less well in a noisy environment. The sensor to be used is then, in particular, a noise pressure meter. Depending on the position, it may also be difficult for the person to process the information. For example, an information message may be difficult to process in a part of a domestic environment, such as a bathroom. Similarly, it may be difficult or more difficult to process the information if the person is not located in or in the vicinity of the livestock building environment, such as abroad, on the water, in a forest, shop or the like. Some details may, for example, be recorded in the form of GPS coordinates. An area can then be selected wherein, if the receiver, i.e. the second communication device, is located in that area, the second mode is chosen by the controller. Other configurations are also possible.

In embodiments, the controller is configured to determine the parameter value as "busy" if the person is busy with one of a predefined group of activities comprising the operation of a component of the livestock farming system, in particular the second communication device, or a device in an information exchange connection with the livestock farming system, in particular the second communication device, and "not busy" if that is not the case. The "busy" parameter value, or a technical equivalent thereof, relates to situations in which it is establishable that the receiving person is busy with an activity that requires his attention. This can be established, for example, by determining whether the person is operating the second communication device, such as by operating buttons or entering information. Alternatively or additionally, it may be establishable that the person is busy with a different activity, such as, in particular, the operation of a device directly or indirectly connected to the second communication device, such as a different device of the livestock farming system, particularly a feed device, feed management computer, etc. For this purpose, the controller can receive operating signals and allocate the "busy" or "not busy" parameter value on the basis thereof. Depending on this parameter value, the information message can then be sent, i.e. directly and undelayed, or delayed, or to a different receiver, etc. A clear example of this relates to the operation of a computer as the second communication device. The computer is then, in particular, a management computer which is intended and configured to manage the livestock farming system. This may relate to a desktop computer or laptop computer, but also variants thereof such as a laptop computer or tablet computer, or even a smartphone with one or more "apps". If the second communication device establishes that the person is entering information, or is processing other information or otherwise using the communication device, such as photographing, phoning or listening to music, the controller can choose the second mode.

The communication system is not particularly restricted. In particular, the communication system comprises Bluetooth®, ZigBee®, Wi-Fi, a mobile telephone connection or Internet connection. By means of communication systems of this type, an efficient information transfer is possible under many circumstances and there is also a wide variety of possibilities in the manner of transfer. For example, mobile telephone connections and also Internet connections have an extensive coverage and, due to the many available extras, such as sensors and applications ("apps"), they are very suitable for use in the present invention.

In embodiments, the second communication device comprises a so-called "wearable", such as a mobile telephone, a PDA, a laptop, a smart watch, smart glasses or a tablet computer. Second communication devices of this type are simply wearable on the person. In addition, more and more devices of this type are already provided as standard with one or more sensors that are useful in the context of the present invention, such as a camera, an accelerometer, etc., so that this sensor can be used with a simple software program (or "app") to determine one or more parameter values. Obviously, it is also possible to provide one or more dedicated sensors on the device, or to provide an alternative communication device, such as a pager or even a camera with communication means.

The invention will be explained below with reference to the drawing, wherein the single FIGURE shows a schematic view of an embodiment of a livestock farming system according to the invention.

FIG. 1 shows a schematic view of a livestock farming system 1 according to the invention. The livestock farming system 1 is partially provided in a livestock building 2.

The livestock building 2 comprises a free-range livestock building 3, for example for cows 4, or also (variants not shown here) beef cattle, chickens, pigs, etc. A feeding rack is denoted by 5, behind which feed 6 is pushed by the feed pusher 7 with a transmitter 8 which is connected to a controller 9 via the first communication device 10.

Here, the livestock farming system shown furthermore comprises an autonomous mower 11 which produces feed outside the livestock building environment by mowing by means of a cutting bar 12, and a transmitter 13.

The livestock building 2 furthermore comprises a so-called feed kitchen 14 in which a plurality of feed bales 15 can be mixed by means of a gripper 16 on a travelling crane 17 in a feed-mixing device (not shown). A transmitter is denoted by 18.

The livestock building 2 furthermore comprises a calf pen 19, in which a calf 20 can be fed by an automatic calf feeder 21 with a transmitter 22.

A first person carrying a second communication device 28 and a heart rate monitor 29 is denoted by 27. A sound pressure meter is denoted by 30 and a communication satellite by 31.

A second person 32 carries a third communication device 33. The livestock farming system 1 thus comprises a communication system which in turn comprises at least the communication devices 10 and 28, and optionally also the third communication device 33. Here, the livestock farming system shown furthermore comprises a feed pusher 7, an autonomous mower 11, a feed-gripping device 16, 17, an automatic calf feeder 21, their respective transmitters 8, 13, 18 and 22, the controller 9 itself, and also the heart rate monitor 29 and the sound pressure meter 30. For the sake of clarity, it should be noted here that numerous other combinations and components are possible, such as an automatic chicken feeder instead of the combination of feed pusher 7, mower 11, feed-gripping device 16, 17, and automatic calf feeder 21, and/or, for example, a blood pressure monitor instead of the heart rate monitor 29. Even the second communication device 28 itself could also be used as the sensor, for example if it establishes that the first person 27 is busy with a task. It is furthermore noted that one or more of the transmitters 8, 13, 18 and 22 may also be transceivers in order, for example, to be able to receive instructions from the controller 9.

The aforementioned components of the livestock farming system 1 can therefore be provided on or in a livestock building 2, but also outside such as on a meadow, for example the mower 11.

The operation of the livestock farming system will be explained in detail below. If, for example, the feed pusher 7 notes that the feed 6 has run out, a mechanical or other fault has occurred, etc., the feed pusher will transmit corresponding information via the transmitter 8 to the controller. The controller 9 will then send an information message to a supervising first person 27, via the first and second communication devices 10 and 28, for example a GSM transmitter or a mobile telephone. The communication satellite 31 can be used here. Alternatively, 10 is a Bluetooth® or Wi-Fi transmitter, and 28 is a Bluetooth® or Wi-Fi receiver, or a different communication system, and the satellite 31 is not necessary. Obviously, it is also possible to design the controller 9 as a distributed controller, wherein the first communication device is distributed over the devices to be controlled so that the transmitters 8, 13, 18 and/or 22 could also be regarded as the first communication device, instead of or in addition to the component 10.

The aforementioned message may differ in type and priority. Thus, a lack of feed 6 will have a much higher priority than, for example, an information message that a battery (not separately shown) of the feed pusher 7 is half-discharged. A fault in the feed-gripping device 16, 17 will also often be less relevant than a fault in an automatic calf feeder 21, given that calves are considerably more vulnerable and disruption early in their life can severely damage their health. It may then be of great importance to ensure as well as possible that the first person 27 who receives the information message processes the information well and takes any necessary action.

All manner of circumstances may influence that information-processing and action-taking capability, such as an increased stress level and a high level of ambient noise. In order to be able to take account of this, the system 1 here comprises, for example, a heart rate monitor 29 and a sound pressure meter 30 which are actively connected to the controller, either directly or via at least the second communication device. If, for example, the heart rate monitor measures a heart rate of more than 100 beats per minute, the system 1, in particular the second communication device 28 or controller 9, concludes that the first person 27 is not readily able to process the information to be sent, or information possibly already sent but not yet made cognizable. Alternatively or additionally, if the sound pressure level as measured by the sound pressure meter 30 is above 70 dB(A), the system, in particular the second communication device 28 or controller 9, concludes that the first person 27 is not readily able to process the information to be sent. Other values for the parameters are obviously possible, as well as other parameters, which then require associated sensors. The posture of the body and head has already been mentioned above.

It is also possible to establish whether the first person 27 is "busy", since the system 1 looks at the operation of the controller 9, the second communication device 28 or possibly one of the feed-related devices 7, 11, 16, 17 or 21 actively connected to the controller 9. In this last case, it may be advantageous to link the position of the first person 27, as to be determined, for example, by means of GPS coordinates of the second communication device 28, to the position of the relevant device. If the first person 27 is "busy", the controller can similarly establish that the first person is not readily able to process the information message well and quickly.

If the system 1 has established that the first person 27 is not readily able to process the information to be sent or sent, it may decide to delay the sending or communicating (such as showing on a telephone screen) until the parameter values lie within a permitted range. This may apply, for example, to non-emergency information messages. For emergency messages, such as alarms and faults, the system 1 can alternatively choose to send the information message to an alternative, in this case a second person 32, who carries a third communication device 33, such as a mobile telephone or tablet computer.

The embodiment shown is not intended to be limiting, but only to clarify the invention. The scope of protection is determined on the basis of the attached claims.

The invention claimed is:

1. A livestock farming system for use in connection with feed for livestock and comprising:
   at least one autonomous feed-related device configured to carry out a livestock-related action on the feed;
   a controller configured to control the livestock farming system and generate information messages; and
   a communication system comprising a first communication device at least configured to send the information messages, and a second communication device at least configured to receive the information messages that have been sent by the first communication device and make them cognizable to a person,
   wherein the livestock farming system is configured to define a parameter value of a parameter relating to the condition of the person,
   wherein the controller is configured to perform at least one operation of sending the information message, and making the information message cognizable to the person depending on the defined parameter value,
   wherein the parameter is a physical condition parameter of the person, and the livestock farming system comprises a sensor actively connected to the controller to measure the parameter value of the person, and
   wherein the parameter comprises a stress level parameter, and the sensor comprises at least one of an accelerometer, a heart rate monitor, a blood pressure monitor and a respiration frequency monitor.

2. The livestock farming system as claimed in claim 1, wherein the at least one autonomous feed-related device comprises at least one of:
   a harvester;
   a feed pusher;
   a feed-combining device;
   a feed-mixing device; and
   a feed-dispensing device.

3. The livestock farming system as claimed in claim 1, wherein the controller is configured to send the information message from the first communication device to the second communication device and to make the information message cognizable on the second communication device to the person in a first mode for non-delayed communication to the second communication device when the defined parameter value meets a first criterion, and to perform at least one operation of sending the message from the first communication device to the second communication device and making said message cognizable to the person on the second communication device in a second, different mode when the defined parameter value meets a second, different criterion.

4. The livestock farming system as claimed in claim 3, wherein the first criterion comprises that the defined parameter value has a predefined value or lies in a predefined interval, and the second criterion comprises that the parameter value does not have the predefined value or lies outside that interval.

5. The livestock farming system as claimed in claim 3, wherein the controller is configured in the second mode to delay sending the information message from the first communication device or communicating the information message to the person until either the defined parameter value meets the first criterion, or until a third criterion is met.

6. The livestock farming system as claimed in claim 3, wherein the controller is configured in the second mode to send the message to a different, third communication device.

7. The livestock farming system as claimed in claim 1, wherein the controller is configured to send information messages with different priority, and the controller is configured to send the information messages from the first communication device to the second communication device or to communicate said messages on the second communication device depending on the priority.

8. The livestock farming system as claimed in claim 1, wherein the parameter value comprises an ambient parameter value of the person, and wherein the sensor comprises a sound pressure meter.

9. The livestock farming system as claimed in claim 1, wherein the controller is configured to determine the parameter value as busy when the person is busy with one of a predefined group of activities comprising the operation of a component of the livestock farming system, or a device in an information exchange connection with the livestock farming system, and "not busy" when the person is not busy with one of a predefined group of activities.

10. The livestock farming system as claimed in claim 1, wherein the communication system comprises a Bluetooth connection, a Zigbee connection, a mobile telephone connection or Internet connection.

11. The livestock farming system as claimed in claim 1, wherein the second communication device is a mobile telephone, a PDA, a laptop, a smart watch, smart glasses or a tablet computer.

12. A livestock farming system for use in connection with feed for livestock and comprising:
   at least one autonomous feed-related device configured to carry out a livestock-related action on the feed;

a controller configured to control the livestock farming system and generate information messages; and
a communication system comprising a first communication device at least configured to send the information messages, and a second communication device at least configured to receive the information messages that have been sent by the first communication device and make them cognizable to a person,
wherein the livestock farming system is configured to define a parameter value of a parameter relating to the condition of the person,
wherein the controller is configured to perform at least one operation of sending the information message and making the information message cognizable to the person depending on the defined parameter value,
wherein the parameter is a physical condition parameter of the person, and the livestock farming system comprises a sensor actively connected to the controller to measure the parameter value of the person, and
wherein the parameter value comprises an ambient parameter value of the person, and the sensor comprises a sound pressure meter.

13. The livestock farming system as claimed in claim 12, wherein the at least one autonomous feed-related device comprises at least one of:
a harvester;
a feed pusher;
a feed-combining device;
a feed-mixing device; and
a feed-dispensing device.

14. The livestock farming system as claimed in claim 12, wherein the controller is configured to send the information message from the first communication device to the second communication device and to make the information message cognizable on the second communication device to the person in a first mode for non-delayed communication to the second communication device when the defined parameter value meets a first criterion, and to perform one operation of sending the message from the first communication device to the second communication device and making said message cognizable to the person on the second communication device in a second, different mode when the defined parameter value meets a second, different criterion.

15. The livestock farming system as claimed in claim 14, wherein the first criterion comprises that the defined parameter value has a predefined value or lies in a predefined interval, and the second criterion comprises that the parameter value does not have the predefined value or lies outside that interval.

16. The livestock farming system as claimed in claim 14, wherein the controller is configured in the second mode to delay sending the information message from the first communication device or communicating the information message to the person until either the defined parameter value meets the first criterion, or until a third criterion is met.

17. The livestock farming system as claimed in claim 14, wherein the controller is configured in the second mode to send the message to a different, third communication device.

18. The livestock farming system as claimed in claim 12, wherein the controller is configured to send information messages with different priority, and the controller is configured to send the information messages from the first communication device to the second communication device or to communicate said messages on the second communication device depending on the priority.

19. The livestock farming system as claimed in claim 12, wherein the parameter comprises a stress level parameter, and the sensor comprises at least one of an accelerometer, a heart rate monitor, a blood pressure monitor and a respiration frequency monitor.

20. The livestock farming system as claimed in claim 12, wherein the controller is configured to determine the parameter value as busy when the person is busy with one of a predefined group of activities comprising the operation of a component of the livestock farming system, or a device in an information exchange connection with the livestock farming system, and "not busy" when the person is not busy with one of a predefined group of activities.

* * * * *